United States Patent [19]

Edwards et al.

[11] Patent Number: 5,565,198

[45] Date of Patent: Oct. 15, 1996

[54] ZONA PELLUCIDA AS A GROWTH STIMULANT

[76] Inventors: John F. Edwards, Texas A&M University, College of Veterinary Medicine, Dept. of Veterinary Pathobiology, College Station, Tex. 77843-4467; David P. Hutcheson, Texas A&M University, Agricultural Research and Extension Center, 6500 Amarillo Blvd., West Amarillo, Tex. 79106; Ronald D. Randel; Francis M. Rouquette, Jr., both of Texas A&M University, Agricultural Research & Extension Center, P.O. Drawer E, Overton, Tex. 76584

[21] Appl. No.: 370,347

[22] Filed: Jan. 9, 1995

Related U.S. Application Data

[63] Continuation of Ser. No. 192,772, Feb. 7, 1994, abandoned, which is a continuation of Ser. No. 789,746, Nov. 8, 1991, abandoned.

[51] Int. Cl.$^6$ .................. A61K 39/00; A61K 38/16; C07K 1/00; C07K 16/00
[52] U.S. Cl. .................. 424/184.1; 514/8; 514/12; 530/397; 530/855; 530/387.1; 530/385; 530/398
[58] Field of Search .................. 514/8, 12; 424/85.9, 424/184.1; 530/387, 385, 348, 399, 855, 387.1

[56] References Cited

U.S. PATENT DOCUMENTS

| | | | |
|---|---|---|---|
| 3,992,520 | 11/1976 | Gwatkin | 424/85 |
| 4,469,671 | 9/1984 | Zimmerman et al. | 424/16 |
| 4,795,634 | 1/1989 | Grimes et al. | 530/387 |
| 4,996,297 | 2/1991 | Dunbar | |

OTHER PUBLICATIONS

Schanbacher, J. Animal Sci. 59:1621 (1984).
Perry, et al., J. Animal Sci. 31:789 (1970).
Utley et al., J. Animal Sci. 34:339 (1972).
Hill, et al., J. Animal Sci. 66:2435 (1988).
Faulkner, D. B., et al., J. Animal Sci. 67:1907 (1989).
Simms, et al., J. Animal Sci. 66:2736 (1989).
Dunbar, et al., Biochemistry 19:356 (1980).
Gwatkin, et al., Gamete Research 3:217 (1980).
Adams, T. E., et al., *J. Animal Sci.* 68:3079–3085 (1990).
Adams, T. E. and Adams, B. M., *J. Animal Sci.* 68:2793–2802 (1990).
DeHaan et al. 1990. J. Anim. Sci. 68:2198–2207.

*Primary Examiner*—James C. Housel
*Assistant Examiner*—N. M. Minnifield
*Attorney, Agent, or Firm*—Barnes & Thornburg

[57] ABSTRACT

*Zona pellucida* is useful for growth stimulation in animals and especially in female ruminants such as heifers. Immunization of heifers with *Zona pellucida* obtained from young pig ovaries leads to increased weight gains that are comparable to, or exceed the weight gain achieved with by other growth stimulants given to cattle, such as steroids, antibiotics or ionophores. *Zona pellucida* treatment results in longer-lasting weight gain response than that achieved with conventional growth stimulants and results in less frequent cattle handling and decreased production costs.

19 Claims, No Drawings

ZONA PELLUCIDA AS A GROWTH STIMULANT

This application is a continuation of application Ser. No. 08/192,772, filed Feb. 7, 1994, now abandoned, which is a continuation of application Ser. No. 07/789,746 filed Nov. 8, 1991 now abandoned.

BACKGROUND OF THE INVENTION

This invention is related to growth stimulants for animals and, more particularly, to a complex glycoprotein growth stimulant derived from mammalian *Zona pellucida* for use in female ruminants such as heifers.

Innovations in farming and ranching have led to an industry that provides not only a livelihood for farmers and ranchers, but also, abundant quantities of food for the world's growing population and its increasing need for animal protein. Advances in food production have occurred as a result of technologic improvements in agriculture and animal science.

Raising domestic livestock, such as bovines (cattle), for red meat or beef production is an important part of producing food for the industrialized world's population. Usually, cattle intended for meat production are allowed to graze pastures until a desired weight is reached, and then additional weight is added in a feedlot prior to slaughter. Heifers fed in feedlots gain less weight than their male counterparts (steers or bulls), and this reduced weight gain increases the production cost for feeding heifers to acceptable weights for desired carcass quality.

Numerous practices are used in feedlot situations to decrease production costs for beef producers. Anabolic agents have been used for more than 20 years to promote and improve growth and to manipulate the metabolism of protein, carbohydrate, lipid and energy in cattle; see, for example, the article by Schanbacher, J. Animal Sci. 29:490 (1984). In commercial feedlots, heifers are implanted with and fed growth stimulants; see, for example, the articles by DeHaan et. al., J. Animal Sci. 68:2198 (1990), and Perry et. al., J. Animal Sci. 31:789 (1970). The implants are steroidal in nature and feed additives used with heifers include steroidal compounds (such as melengesterol acetate), ionophores, and antibiotics.

Antibiotics have been fed in beef cattle rations since the 1940's to improve growth and prevent disease; see, for example, the article by Utley et. al., J. Animal Sci. 34:339 (1972). Ionophores have been fed to cattle since 1977 to promote growth and improve the feed-to-gain conversion ratio. The feed-to-gain conversion ratio is a measurement of the efficiency of feed used to produce a gain in weight. A procedure that causes cattle to gain more weight on less feed has an improved feed-to-gain conversion ratio.

Melengesterol acetate is commonly used as a steroidal feed additive product for heifers and is fed daily in prepared rations; see, for example, the articles by Hill et. al., J. Animal Sci. 66:2435 (1988); Young, et. al., J. Animal Sci. 28:224 (1969); Hawkins et. al., J. Animal Sci. 35:1257 (1972); and Purchas et. al., J. Animal Sci. 33:836 (1971) and J. Animal Sci. 32:628 (1971). Melengesterol acetate is approved to be fed to beef heifers and its use leads to increased weight gain, improved feed efficiency and suppression of estrus (heat) in heifers.

The use of implants is the most effective method of decreasing the production cost of all the practices mentioned above. Implants are used more in the production of red meat in cattle than any other present management system; see, for example, the article by Faulkner et. al., J. Animal Sci. 67:1907 (1989) and Purchas et. al., J. Animal Sci. 32:628 (1971). Using diverse management systems including new and innovative methods, beef producers have been able to reduce production costs.

Presently, cattle may receive implants as many as 5 to 7 times from birth to slaughter; see, for example, the article by Simms, et. al., J. Animal Sci. 66:2736 (1989). Although this procedure results in improved feed-to-gain conversion, it requires frequent cattle handling.

There are other disadvantages to the use of implants and feed additives. Some foreign markets object to meat from heifers in which exogenous hormone supplementation has been used. For example, on Jan. 1, 1989, the European Economic Community (EEC) imposed a ban on American beef, claiming that growth hormones given to cattle could be a health hazard. The perceived fear of exogenous hormones, although not scientifically substantiated, has a psychological impact on the consumer. In addition, some feed additives may also be toxic if improperly mixed in feeds.

These and other limitations and disadvantages of the prior art are overcome by the present invention, and the use of *Zona pellucida* as an improved growth stimulant is provided.

SUMMARY OF THE INVENTION

The present invention employs *Zona pellucida* to provide increased weight gain in animals such as female ruminants. In a preferred embodiment, porcine *Zona pellucida* is administered intramuscularly to heifers to increase weight gain. *Zona pellucida* is preferably obtained by shredding and filtering gilt (young pig) ovaries. *Zona pellucida* antigen is lyophilized and reconstituted prior to administration. The weight gain achieved with *Zona pellucida* is at least comparable to, or exceeds the weight gain achieved by other growth stimulants. *Zona pellucida* may be administered as a single injection or as multiple injections. Fewer treatments would result in decreased production costs. Further, treatment with *Zona pellucida* increases weight gains for several months, obviating the need for repeated treatments.

These and other advantages of the present invention will become apparent from the following detailed description.

DETAILED DESCRIPTION OF THE INVENTION

The present invention involves the use of *Zona pellucida* antigen immunization to enhance weight gain in animals. A preferred embodiment of the present invention involves the use of *Zona pellucida* antigen immunization to enhance weight gain in ruminants, more preferably in bovines, and most preferably bovines of female gender (e.g.: heifers). Preferably, *Zona pellucida* antigens are delivered in an oil-and-water emulsion and preferably injected intramuscularly.

*Zona pellucida* is a complex extracellular glycoprotein matrix surrounding the mammalian oocyte. See, for example, the chapter by Skinner and Dunbar, in Talwar, G.P. ed.; *Immunological Approaches to Contraception and Promotion of Fertility*, pp. 251–268 (1986). The *Zona pellucida* matrix is formed during the early stages of oocyte growth and follicular cell differentiation. *Zona pellucida* plays an integral part in the fertilization process by acting very much like a semi-permeable barrier to spermatozoa penetration. The sperm must first bind to *Zona pellucida*. Subsequently, sperm penetration occurs by limited hydrolysis of *Zona pellucida* components. In this fashion, *Zona pellucida* prevents polyspermy—ovum fertilization by more than one sperm cell. After fertilization, the *Zona pellucida* remains intact and protects the developing embryo until implantation.

*Zona pellucida* have been used as an antifertility agent in animals as described more fully in U.S. Pat. No. 3,992,520. U.S. Pat. No. 4,996,297 teaches the use of recombinantly-expressed *Zona pellucida* antibodies polypeptides for immunocontraception. In this manner, *Zona pellucida* may serve as a safer alternative to harsher birth control procedures, such as surgical intervention. However, neither of these patents teach or suggest the use of *Zona pellucida* to stimulate growth in animals.

As used herein, the term "*Zona pellucida*" is intended to include the complex extracellular glycoprotein matrix surrounding the oocyte as described above. It is also intended to include the deglycosylated or deglycated proteins that are included in the matrix; "deglycosylated protein" means the protein backbone of a glycoprotein molecule lacking some or all of its carbohydrate moieties. The term "deglycated protein" may also be used to define the protein backbone of a glycoprotein molecule lacking some or all of its carbohydrate moieties.

The term "*Zona pellucida*" is also intended to include polypeptides having essentially the same amino acid sequence as the naturally occurring and recombinant *Zona pellucida* protein(s) and any analogs thereof. The term "analogs" is intended to include proteins or polypeptides which differ from natural *Zona pellucida* protein by addition, deletion or substitution of one or more amino acids, providing that polypeptide demonstrates substantially the antigenic, biologic and growth stimulant activity of natural *Zona pellucida*.

In a preferred embodiment, use of *Zona pellucida* immunization alone, or with an adjuvant or adjuvant(s) to improve weight gain in heifers obviates the need for administration of exogenous hormone or hormone-like compounds. This is important since it is the perception of some consumers and foreign markets (EEC) that hormonal feed additives or implants leave hormone residues in the heifers. In alternative embodiments, *Zona pellucida* may be administered with hormone or hormone-like compounds or other growth stimulants (with or without an adjuvant) to increase weight gain.

The effective period of enhanced weight gain with *Zona pellucida* is longer than any existing methods involving exogenous hormone or hormone-like compound supplementation. Conventional one-time hormone supplementation causes weight gains for up to 60 to 200 days and depends on the implant used. In accordance with the teachings of the present invention, intramuscular injection of *Zona pellucida* into heifers may stimulate weight gain for more than 300 days; thus, cattle handling and associated production costs are reduced.

*Zona pellucida* causes weight gains at least comparable to or exceeding those achieved with conventional hormone treatment or growth stimulants. As a non-limiting example of the present invention, *Zona pellucida* injected intramuscularly into weaned heifers causes a 16.2% improved weight gain when compared to untreated heifers. In comparison, by using two commercially available steroid implants in weaned heifers, a 12 to 18% weight gain may be realized. *Zona pellucida* immunization produces weight gains comparable to or exceeding those obtained with exogenous hormone or growth stimulants. It is presently believed similar weight gains will occur in other ruminants or animals.

However, *Zona pellucida* immunization offers a safe, more cost-effective alternative to existing hormone implants or supplementation for production of beef in a marketplace which demands low-cost beef and for consumers who are concerned about the use of exogenous hormone residues or growth stimulants.

Although the present invention contemplates the use of *Zona pellucida* given alone or in combination with an adjuvant, alternative embodiments include coadministration of hormone or hormone-like compounds or other growth stimulants and/or antibiotics with the *Zona pellucida* and/or adjuvant.

*Zona pellucida* PREPARATION

Isolation of *Zona pellucida* is achieved by a modification, as described below, of known procedures; see for example, the articles by Dunbar et al., Biochemistry 19:356–365 (1980), and Gwatkin et. al, Gamete Research 3:217–231 (1980). Large numbers of ovaries are collected from prepubertal market-weight gilts (female pigs) at slaughter and are frozen at −4° C. to −20° C. Processing of ovaries is achieved by passing the frozen ovaries three times through a standard meat tenderizer. The tenderizer blades are bathed continually with a citrate buffered saline solution while grating the ovaries. At all times in the process, ovaries and cortical tissue including *Zona pellucida* that is removed from the ovaries are maintained in a citrate buffered saline solution (pH 7.2) containing 12 mM sodium citrate and 12 mM ethylene glycol tetraacetic acid (EGTA). Shredded ovaries are washed three times over a coarse filter funnel and discarded. The wash fluid and the fluid in which ovaries were grated are combined in plastic beakers.

The fluid is run sequentially through 1000, 500, 200, 150 and 75 micron nylon mesh filters. The material held back by each filter is back-washed from the screen and refiltered three times and the filtrate is collected and passed through the next smaller filter. The material collected by the 75 micron screen filter is then collected. This material is Dounce homogenized six times and filtered through a 50 micron screen. The material caught by the 50 micron screen contains the *Zona pellucida* antigen (without the ova) and may be used in accordance with the teachings of the present invention.

Approximately 300 ova and their *Zona pellucida* are obtained from each ovary. The product contains some intact eggs surrounded by *Zona pellucida*, but greater than 98% of the product consists of broken *Zona pellucida* stripped of the egg. This material is freeze dried or lyophilized prior to emulsification. Usually, 5 ml of antigen preparation is freeze dried overnight in a standard lyophilizing unit such as commonly obtainable from Virtis Co., Gardner, N.J., 12525.

VACCINE PREPARATION

A weighed dose of lyophilized *Zona pellucida* is placed in a sterile mortar, ground to a fine powder, and emulsified in an appropriate pharmaceutical carrier for use as an injectable solution or suspension. Appropriate carriers include, but are not limited to emulsions of phosphate buffered saline with TWEEN® 80 (polyoxyethylene sorbitan monooleate, Sigma Chemical Co., St. Louis, Mo., U.S.A.) (Registered mark of ICI Americas, Inc.) and SPAN® 80 (sorbitan monooleate, Sigma Chemical Co., St. Louis, Mo., U.S.A.) (Registered mark of ICI Americas, Inc.) in peanut oil, squalene oil and hexadecane. In a preferred embodiment, Zona pellucida is emulsified in a modified formulation of T1501 tetronic block copolymer adjuvant carrier (see, for example, the article by Woodard, Lab. Animal Sci. 39:222 [1989]) which is a mixture containing by volume:

10 parts hexadecane 7 parts Tween® 80

3 parts Span® 80

3 parts glycerol trioleate

When a smooth flowing suspension of powder and carrier is obtained, it is emulsified in an equal volume of sterile, physiological phosphate buffered saline solution (pH 7.2). The vaccine is maintained at 4° C. until used.

A broad dose range of Zona pellucida, from about 25 milligrams to about 100 milligrams, is emulsified in a pharmaceutically acceptable carrier of about 1 ml to 2 ml. Those skilled in the art will recognize that smaller or larger concentrations of Zona pellucida may be emulsified depending on the Zona pellucida purity and desired biological effect as noted later herein. This oil-in-saline suspension has an adjuvant effect; that is, it may non-specifically augment the host's immune response.

While the preferred route of administration of Zona pellucida is via intramuscular injection, Zona pellucida can also be administered subcutaneously, intradermally, or via implants. In accordance with the teachings of the present invention, the route, dosage and timing of Zona pellucida administration will vary depending on factors such as animal age, health condition, desired weight gain, and other variables which can be readily ascertained and adjusted (all in accordance with the teachings of present invention) by a person having ordinary skill in the art after familiarizing himself or herself with the teachings of this invention. In accordance with the teachings of the present invention, about 50 to about 400 milligrams (mg) of Zona pellucida may be administered. Smaller concentrations may be administered depending on the purity or activity of the Zona pellucida. In a preferred embodiment, three vaccinations of Zona pellucida are given intramuscularly (100, 150 and 200 milligrams), suspended in a total volume of 2 milliliters of adjuvant carrier solution. The three vaccinations are separated by approximately 4-week intervals. Administration of Zona pellucida commences at the time the producer desires to begin the growth stimulating process.

It may be desirable to administer adjuvant(s) (other than the oil-in-saline adjuvant) in conjunction with Zona pellucida. Adjuvants are substances that can be used to non-specifically augment a specific immune response. Preferably, the adjuvant carrier and the Zona pellucida are mixed prior to presentation to the animal's immune system. Alternatively, adjuvants may be administered before or after Zona pellucida administration.

Adjuvants can be loosely divided into several groups based on their composition. These groups include oil adjuvants (for example, Freund's complete and incomplete adjuvants and T1501 tetronic block copolymer), mineral salts (for example, $AlK(SO_4)_2$, $AlNa(SO_4)_2$, $AlNH_4(SO_4)$, silica, alum, $Al(OH)_3$, $Ca_3(PO_4)_2$, Kaolin, and carbon), polynucleotides (for example, poly IC and poly AU acids) and certain natural substances (for example, wax D from *Mycobacterium tuberculosis*, trehalose dimycolate, sorbitan trioleate and glycerol trioleate, as well as substances found in *Corynebacterium parvum*, *Bordetella pertussis*, and members of the genus Brucella). In a preferred embodiment, an effective amount of *Bordetella pertussis* toxin is intravenously administered concurrently with the second administration of Zona pellucida. As a non-limiting example, 10 micrograms of pertussis toxin may be administered.

The scope of the present invention is intended to include varying the following: the number of administrations; the timing between subsequent administrations; the dosage; the route of administration; the source of Zona pellucida; the purity of Zona pellucida; and the form of Zona pellucida. As a non-limiting example, one injection may be administered or, alternatively, two injections may be administered over a six-month period. Alternatively, multiple injections may be administered at varying time periods. As non-limiting examples, Zona pellucida could be obtained from sources other than gilts. Zona pellucida might be synthesized or produced through recombinant techniques. The form of Zona pellucida might also be modified such as by using purified Zona pellucida glycoproteins, glycoprotein subunit(s), and solubilized or unsolubilized Zona pellucida.

The following example specifically illustrates one embodiment of the invention, but does not limit the pharmaceutical composition or method of treatment aspects of the present invention. The following specific example describes treatment procedures which are generally applicable to the present invention.

EXAMPLE

Weaned, crossbred beef heifer calves were paired based on size, birth weight, and birth date. The heifer pairs were randomly allocated into a Zona pellucida or a control (no Zona pellucida) group. The heifers were grazed on pasture for 207 days and then fed in a feedlot for 112 days. Zona pellucida administration commenced at the time that the heifers began grazing on pasture. The heifers were vaccinated three times at four-week intervals using doses of 100, 150 and 200 milligrams of Zona pellucida in adjuvant carrier at each vaccination. Table 1 represents the gains for the pasture and feedlot phase.

TABLE 1

|  | Control | Treated | Days |
| --- | --- | --- | --- |
| Gain on pasture | $238.6 \pm 28.7^a$ | $275.0 \pm 27.2$ | 207 |
| Gain in feedlot | $267.8 \pm 14.6$ | $321.2 \pm 13.9$ | 112 |
| Total Gain | $508.9 \pm 32.3$ | $591.2 \pm 30.6$ | 319 | a = standard error

During the 112-day feedlot period, control heifers (those not receiving Zona pellucida) achieved an average weight gain of 267.8 pounds. Heifers receiving Zona pellucida achieved an average weight gain of 321.2 pounds, which represented a 19.9% increase in weight during the feedlot period. The weight gain in the feedlot for the Zona pellucida-treated animals was significantly ($P<0.02$) improved.

The total average weight gain in the 319-day pasture and feedlot period was also enhanced in these heifers which received Zona pellucida. Heifers not receiving Zona pellucida achieved an average weight gain of 508.9 pounds. Heifers receiving Zona pellucida achieved an average weight gain of 591.2 pounds. Zona pellucida, therefore, produced a 16.2% increase in total weight during the combined pasture and feedlot periods. The overall total weight gain was greater for the Zona pellucida-treated cattle ($P<0.09$).

Table 2 illustrates the average daily gains for the heifers and their feed-to-gain conversion ratio during the feedlot phase. Treated cattle had a 6.9% better feed-to-gain conversion ratio. The feed-to-gain conversion was better ($P<0.20$, i.e. feed-to-gain was better in 80% of cases) for the *Zona pellucida*-treated cattle. Improvement in total gain and the improved feed-to-gain ratio are the most significant factors in decreasing production cost.

TABLE 2

| Feedlot | Control | Treated |
|---|---|---|
| Feed-to-Gain | 5.95 ± 0.22 | 5.54 ± 0.21 |
| Daily gain, lb/d | 2.39 ± 0.13[a] | 2.87 ± 0.12 | a = standard error

The carcass data indicated a heavier (P<0.10) carcass weight with no changes in the other variables measured (Table 3). Thus, this is another good indication of true weight gain produced from the invention.

TABLE 3

| Carcass Variable | Control | Treated |
|---|---|---|
| Hot carcass Weight | 590.3 ± 15.4[a] | 635.6 ± 17.5 |
| Dressing, % | 61.98 ± 0.52 | 61.23 ± 0.49 |
| Ribeye area, sq. in. | 11.73 ± 0.39 | 10.84 ± 0.37 |
| Prelim yield grade | 2.89 ± 0.25 | 3.22 ± 0.24 |
| Adj'd prelim yield gr. | 2.79 ± 0.26 | 3.29 ± 0.25 |
| Kidney pelv. hrt. fat | 2.06 ± 0.09 | 2.00 ± 0.08 |
| Marbling score | 3.33 ± 0.11 | 3.51 ± 0.11 | a = standard error

Many other variations and modifications may be made in the techniques hereinbefore described, by those having experience in this technology, without departing from the concept of the present invention. Accordingly, it should be clearly understood that the methods referred to in the foregoing description are illustrative only and are not intended as limitations on the scope of the invention.

What is claimed is:

1. A method for enhancing weight gain in a meat producing female ruminant species, said method comprising administering a composition comprising *Zona pellucida* and a pharmaceutically acceptable carrier to said ruminant species in an amount effective to enhance weight gain.

2. A method according to claim 1 wherein said ruminant species is a bovine.

3. A method according to claim 1 wherein said pharmaceutically acceptable carrier is selected from the group consisting of hexadecane, TWEEN® 80 (polyoxyethylene sorbitan monooleate), SPAN® 80 (sorbitan monooleate), glycerol trioleate and physiological phosphate buffered saline.

4. A method according to claim 1 wherein said composition further comprises an adjuvant.

5. A method according to claim 4 wherein said adjuvant is a toxin from *Bordetella pertussis*.

6. A method according to claim 1 further comprising the step of administering an adjuvant intravenously.

7. A method according to claim 6 wherein said adjuvant is administered intravenously as a 10 microgram dose.

8. A method according to claim 1 wherein the composition comprises 25 to 400 milligrams of *Zona pellucida* per dose.

9. A method according to claim 1 wherein the composition comprises 100 to 200 milligrams of *Zona pellucida* per dose.

10. A method according to claim 1 wherein the composition is administered intramuscularly.

11. A method according to claim 1 wherein the composition is administered in multiple doses.

12. A method for improving the feed to gain conversion ratio in a meat producing female ruminant species, said method comprising administering a composition comprising *Zona pellucida* and a pharmaceutically acceptable carrier to said ruminant species in an amount effective to increase the gain in ruminant weight per weight of feed consumed.

13. A method according to claim 12 wherein said ruminant species is a bovine.

14. A method according to claim 12 wherein said pharmaceutically acceptable carrier is selected from the group consisting of hexadecane, TWEEN® 80 (polyoxyethylene sorbitan monooleate), SPAN® 80 (sorbitan monooleate), glycerol trioleate and physiological phosphate buffered saline.

15. A method according to claim 12 wherein said composition further comprises an adjuvant.

16. A method according to claim 12 further comprising the step of administering an adjuvant intravenously.

17. A method according to claim 16 wherein said adjuvant is administered intravenously as a 10 microgram dose.

18. A method according to claim 12 wherein the composition comprises 25 to 400 milligrams of *Zona pellucida* per dose.

19. A method according to claim 12 wherein the composition is administered intramuscularly.

* * * * *